US009662305B2

(12) United States Patent
Selley (10) Patent No.: US 9,662,305 B2
(45) Date of Patent: *May 30, 2017

(54) USE OF BUCILLAMINE IN THE TREATMENT OF GOUT

(71) Applicant: REVIVE THERAPEUTICS INC., Vaughan (CA)

(72) Inventor: Michael L. Selley, South Turramurra (AU)

(73) Assignee: Revive Therapeutics Inc., Vaughan, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/855,951

(22) Filed: Sep. 16, 2015

(65) Prior Publication Data

US 2016/0000738 A1    Jan. 7, 2016

Related U.S. Application Data

(63) Continuation-in-part of application No. 14/443,639, filed as application No. PCT/CA2013/050882 on Nov. 19, 2013, now Pat. No. 9,238,018.

(30) Foreign Application Priority Data

Nov. 20, 2012  (AU) ............................... 2012905072

(51) Int. Cl.
*A61K 31/198*    (2006.01)
*A61K 31/165*    (2006.01)
*A61K 31/519*    (2006.01)

(52) U.S. Cl.
CPC .......... *A61K 31/198* (2013.01); *A61K 31/165* (2013.01); *A61K 31/519* (2013.01)

(58) Field of Classification Search
CPC ... A61K 31/198; A61K 31/165; A61K 31/519
USPC .................................................... 514/262.1
See application file for complete search history.

(56) References Cited

FOREIGN PATENT DOCUMENTS

CA       2 652 667 A1   12/2007
WO    WO 2009/085695 A1   7/2009

OTHER PUBLICATIONS

Obayashi et al. Clin. Exp. Nephrol., 2003, 7, 275-278.*
International Search Report and Written Opinion issued in corresponding International PCT Application No. PCT/CA2013/050882.
Lawrence D. Horwitz, Bucillamine: A Potent Thiol Donor with Multiple Clinical Applications, Cardiovascular Drug Reviews, vol. 21, (2003) No. 2, pp. 77-90.
Lawrence R., et al., Estimates of the Prevalence of Arthritis and Other Rheumatic Conditions in the United States, Part II, Arthritis Rheum. Jan. 2008; 58(1): pp. 26-35, doi: 10.1002/art.23176.
Wallace K., et al., Increasing Prevalence of Gout and Hyperuricemia Over 10 Years Among Older Adults in a Managed Care Population, The Journal of Rheumatology, (2004) 31:8, pp. 1582-1587.
Hyon K. Choi, A prescription for lifestyle change in patients with hyperuricemia and gout, Lippincott Williams & Wilkins, (2010), pp. 165-172, DOI:10.1097/BOR.0b013e328335ef38.
Terkeltaub R., et al., Recent developments in our understanding of the renal basis of hyperuricemia and the development of novel antihyperuricemic therapeutics, Arthritis Research & Therapy, vol. 8, Suppl. Apr. 1, 2008,pp. 1-9,, http://arthritis-research.com/contents/8/S1/S4.
Vitart V., et al., SLC2A9 is a newly identified urate transporter influencing serum urate concentration, urate excretion and gout, Nature Genetics, vol. 40, No. 4, Apr. 2008, pp. 437-442.
Doblado, D., et al., Facilitative glucose transporter 9, a unique hexose and urate transporter, American Physiological Society, vol. 297 Oct. 2009, pp. E831-E835, www.ajpendo.org.
Phay J., et al., Cloning and Expression Analysis of a Novel Member of the Facilitative Glucose Transporter Family, SLC2A9 (GLUT9), Short Communication, Genomics 66, 217-220 (2000), doi:10.1006/geno.2000.6195.
Preitner F.M et al., Glut9 is a major regulator of urate homeostasis and its genetic inactivation induces hyperuricosuria and urate nephropathy, PNAS, vol. 106, No. 36 Sep. 2009, pp. 15501-15506, www.pnas.org_cgi_doi_10.1073_pnas.0904411106.
Woodward O., et al., Identification of a urate transporter, ABCG2, with a common functional polymorphism causing gout, PNAS, vol. 106, No. 25 Jun. 2009, pp. 10338-10342.
Common Defects of ABCG2, a High-Capacity Urate Exporter, Cause Gout: A Function-Based Genetic Analysis in a Japanese Population, vol. 1, Issue 5, 5ra11, Nov. 2009 www.ScienceTranslationalMedicine.org.
Campion, E., et al., Asymptomatic Hyperuricemia Risks and Consequences in the Normative Aging Study, The American Journal of Medicine, vol. 82, Mar. 1987. pp. 421-426.
Agudelo, C., et al., Crystal-Associated Arthritis, Clinics in Geriatric Medicine, vol. 14, No. 3, Aug. 1998, pp. 495-513.
John N. Loeb, The Influence of Temperature on the Solubility of Monosodium U rate, Arthritis and Rheumatism, vol. 15. No. 2 (Mar.-Apr. 1972), pp. 189-192.
Martinon, F. et al., Gout-associated uric acid crystals activate the NALP3 inflammasome, Nature, vol. 440, Mar. 2006. pp. 237-241.
Petrilli, V., The inflammasome, autoinflammatory diseases, and gout, ScienceDirect, Joint Bone Spine 74, (2007), pp. 571-576.
Chen, C., et al., MyD88-dependent IL-1 receptor signaling is essential for gouty inflammation stimulated by monosodium urate crystals, The Journal of Clinical Investigation vol. 116, No, 8, Aug. 2006, pp. 2262-2271, http://www.jci.org.
Richette, P., et al., Gout, Seminar, vol. 375, Jan. 2010, pp. 318-328, www.thelancet.com.

(Continued)

*Primary Examiner* — Yevegeny Valenrod
(74) *Attorney, Agent, or Firm* — Haug Partners LLP; William S. Frommer (57) ABSTRACT

Disclosed are pharmaceutical compositions comprising, bucillamine, including bucillamine and allopurinol or colchicine, or pharmaceutically acceptable salts or solvates thereof, together with one or more pharmaceutically acceptable carriers, diluents and excipients. Methods for use of the said compositions in the treatment of gout and metabolic syndrome are also disclosed.

14 Claims, 7 Drawing Sheets

(56) References Cited

OTHER PUBLICATIONS

Chao, J., et al., A Critical Reappraisal of Allopurinol Dosing, Safety, and Effi cacy for Hyperuricemia in Gout, Current Rheumatology Reports, 2009, vol. 11: pp. 135-140.
Becker, M., et al., Clinical Efficacy and Safety of Successful Longterm Urate Lowering with Febuxostat or Allopurinol in Subjects with Gout, J Rheumatol, vol. 36, (2009); pp. 1273-1282, http://www.jrheum.org/content/36/6/1273.
Nanke, Y., et al.m Radiographic repair in three Japanese patients with rheumatoid arthritis treated with bucillamine, Mod Rheumatol, vol. 19, (2009), pp. 681-686, DOI 10.1007/s10165-009-0209-6.
Amersi, F. et al., Bucillamine, a thiol antioxidant, prevents transplantation-associated reperfusion injury, PNAS, vol. 99, Jun. 2002, pp. 8915-8920.
Whitekus, M., et al., Thiol Antioxidants inhibit the Adjuvant Effects of Aerosolized Diesel Exhaust Particles in a Murine Model for Ovalbumin Sensitization, The Journal Immunology, vol. 168, (2002), pp. 2560-2567.
Hiura, T., et al., The Role of a Mitochondrial Pathway in the Induction of Apoptosis by Chemicals Extracted from Diesel Exhaust Particles, The Journal Immunology, vol. 165, (2000), pp. 2703-2711.
Lawrence D. Horwitz, Bucillamine Prevents Myocardial Reperfusion Injury, Journal of Cardiovascular Pharmacology, vol. 38: pp. 859-867.
Wielandt, A., et al., Bucillamine induces glutathione biosynthesis via activation of the transcription factor Nrf2, Biochemical Pharmacology, vol. 72, (2006), pp. 455-462.
Jigorel, E., et al., Differential Regulation of Sinusoidal and Canalicular Hepatic Drug Transporter Expression by Xenobiotics Activating Drug-Sensing Receptors in Primary Human Hepatocytes, Drug Metabolism and Disposition, vol. 34, No. 10, (2006) pp. 1756-1763.
Adachi, T., et al., Nrf2-dependent and -independent induction of ABC transporters ABCC1, ABCC2, and ABCG2 in HepG2 cells under oxidative stress, Journal of Experimental Therapeutics and Oncology, vol. 6, (2007) pp. 335-348.
Van Aubel, R., et al., Human organic anion transporter MRP4 (ABCC4) is an efflux pump for the purine end metabolite urate with multiple allosteric substrate binding sites, Am J Physiol Renal Physiol (2005), vol. 288: pp. F327-F333.
Maher, J., et al., Oxidative and Electrophilic Stress Induces Multidrug Resistance—Associated Protein Transporters via the Nuclear Factor-E2—Related Factor-2 Transcriptional Pathway, Hepatology, Nov. 2007, pp. 1597-1610.
Xu, S., et al., Aryl hydrocarbon receptor and NF-E2-related factor 2 are key regulators of human MRP4 expression, Am J Physiol Gastrointest Liver Physiol (2010), pp. : G126-G135.
Aleksunes, L., et al., Transcriptional Regulation of Renal Cytoprotective Genes by Nrf2 and Its Potential Use as a Therapeutic Target to Mitigate Cisplatin-Induced Nephrotoxicity, The Journal of Pharmacology and Experminental Therapeutics, (2010), vol. 335, No. 1, pp. 2-12.
El-Sheikh, A., et al., Effect of Hypouricaemic and hyperuricaemic drugs on the renal urate efflux transporter, multidrug, resistance protein 4, British Journal of Pharmacology (2008) vol. 155, pp. 1066-1075.
Feher, M.D., et al. Fenofibrate enhances urate reduction in men treated with allopurinol for hyperuricaemia and gout, Rheumatology, (2003) vol. 42, pp. 321-325.
Helpburn, A., et al., Fenobrite: a new treatment for hyperuicaemia and ghout? Annals of the Rheumatic Diseases, (2001), vol. 60, pp. 984-986.
Kiyohar, C., et al., Inverse association between coffee drinking and serum uric acid concentrations in middle-aged Japanese males, British Journal of Nutrition (1999), vol. 82, pp. 125-130.

Choi, K., et al., Coffee, Tea, and Caffeine Consumption and Serum Uric Acid Level: The Third National Health and Nutrition Examination Survey, Arthritis & Rheumatism [Arthritis Care & Research], Jun. 2007, vol. 57, pp. 816-821.
Choi, H., et al., Coffee Consumption and Risk of Incident Gout in Men, Arthritis & Rheumatism, Jun. 2007, vol. 56, pp. 2049-2055.
Balstad, T., et al., Coffee, broccoli and spices are strong inducers of electrophile response element-dependent transcription in vitro and in vivo—Studies in electrophile response element transgenic mice,. Mol. Nutr. Food Res., (2011), vol. 55, pp. 185-197.
Boettler, U., et al., Coffee constituents as modulators of Nrf2 nuclear translocation and ARE (EpRE)-dependent gene expression, Journal of Nutritional Biochemistry (2011), vol. 22,pp. 426-440.
Garcia, J., et al., Hyperuricemia, gout and the metabolic syndrome, Current Opinion in Rheumatology 2008, vol. 20, pp. 187-191.
Inokuchi, T., Increased Frequency of Metabolic Syndrome and Its Individual Metabolic Abnormalities in Japanese Patients With Primary Gout, Journal of Clinical Rheumatology, Apr. 2010, vol. 16, No., pp. 109-112.
Fraile, J., et al., Uric Acid Metabolism in Patients with Primary Gout and the Metabolic Syndrome, Nucleosides, Nucleotides and Nucleic Acids, (2010), vol. 29, pp. 330-334.
Yu, Z., et al., Oltipraz upregulates the nuclear respiratory factor 2 alpha subunit (NRF2) antioxidant system and prevents insulin resistance and obesity induced by a high-fat diet in C57BL/6J mice, Diabetologia (2011), vol. 54, pp. 922-934.
Shin, S., et al., Role of Nrf2 in prevention of high-fat diet-induced obesity by synthetic triterpenoid CDDO-Imidazolide, Eur J Pharmacol, Oct. 2009 ; vol. 620, Nos. 1-3, pp. 138-144. doi:10.1016/j.ejphar.2009.08.022.
Zhou, R., et al., Thioredoxin-interacting protein links oxidative stress to inflammasome activation, Nature immunology,Feb. 2010, vol. 11 No. 2, pp. 136-141.
Tanito, M., et al., Upregulation of thioredoxin system via Nrf2-antioxidant responsive element pathway in adaptive-retinal neuroprotection in vivo and in vitro, Free Radical Biology & Medicine, (2007) vol. 42, pp. 1838-1850.
Colcrys® vs. Unapproved Colchicine, www.urlpharma.com/url_unapproved_drug_Colcrys.aspx.
Malawista, S., et al. The Effect of Pretreatment with Colchicine on the Inflammatory Response to Microcrystalline Urate, Apr. 1965, vol. 62, No. 4., pp. 648-657.
Martinino, F., et al., Gout-associated uric acid crystals activate the NALP3 inflammasome, Nature, Mar. 2006, vol. 440, pp. 237-241.
Stavric, B., Some in Vivo Effects in the Rat Induced by Chlorprothixene and Potassium Oxonate, Pharmacological Research Communication, (1975), vol. 7, No. 2, pp. 117-124.
Hall, I., et al., Substituted Cyclic Imides a Potential Anti-Gout Agents, Life Sciences, (1990), vol. 46, pp. 1923-1927.
Wang, Y., et al., Administration of Procyanidins from Grape Seeds Reduces Serum Uric Acid Levels and Decreases Hepatic Xanthine Dehydrogenase/Oxidase Activities in Oxonate-Treated Mice, Basic & Clinical Pharmacology & Toxicology 2004, vol. 94, pp. 232-237.
Carroll, J., et al., A Simplified Alkaline Phosphotoungstate Assay for Uric Acid in Serum, Clinical Chemisty, (1971), vol. 17, No. 3, pp. 158-160.
Liu-Bryan, R., et al., Innate Immunity Conferred by Toll-like Receptors 2 and 4 and Myeloid Differentiation Factor 88 Expression Is Pivotal to Monosodium Urate Monohydrate Crystal—Induced Inflammation, Arthritis & Rheumatism, Sep. 2005, vol. 52, No. 9, pp. 2936-2946.
Ortiz-Bravo, E., et al., Components Generated Locally as Well as Serum After the Phlogistic Effect of Monosodium Urate Crystals in vivo, The Journal of Rheumatology, (1993), vol. 20, No. 7 pp. 1162-1163.
So, A., et al., A pilot study of IL-1 inhibition by anakinra in acute gout, Arthritis Research & Therapy vol. 9 No. 2, pp. 1-6.
Junnarkar, S., et al., Attenuation of warm ischemia—reperfusion injury in the liver by bucillamine through decreased neutrophil activation and Bax/Bcl-2 modulation, Journal Gastroentrology and Hepatology, (2010), vol. 25, pp. 1891-1899.

(56) References Cited

OTHER PUBLICATIONS

Ben-Chetrit, E., et al., Mechanism of the anti-inflammatory effect of colchicine in rheumatic diseases: a possible new outlook through microarray analysis, Rheumatology Oxford Journal, (2006), vol. 45, pp. 274-282.
Cronstein, B., et al., Colchine Alters the Quantitative and Qualitative Display of Selectins on Endothelial Cells and Neutrophils, The American Society for Clinical Investigation, Inc., Aug. 1995, vol. 96, pp. 994-1002.
Tsuji, F., et al., Effects of bucillamine and N-acetyl-L-cysteine on cytokine production and collagen-induced arthritis (CIA), Clin Exo Immunol (1999), vol. 115, pp. 26-31.
Terkeltaub R., et al. High Versus Low Dosing of Oral Colchicine for Early Acute Gout Flare, Arthritis & Rheumatism, Apr. 2010, vol. 62, pp. 1060-1068.
Richette, P., et al. Colchicine for the treatment of gout, Expert Opinion on Pharmacotherapy, Aug. 2015, vol. 16, No. 11, pp. 2932-2938.

\* cited by examiner

Fig. 1  The effects of bucillamine and allopurinol administration on serum urate levels in hyperuricaemic mice Fig. 2　　The effects of bucillamine and allopurinol administration on the urinary excretion of uric acid Fig. 3     The effects of bucillamine and allopurinol administration on urinary creatinine levels Fig. 4 The effect of the administration of bucillamine on monosodium urate crystal-induced peritoneal neutrophil influx Fig. 5    The effects of bucillamine and colchicine administration on monosodium urate crystal-induced peritoneal neutrophil influx Fig. 6  The effect of bucillamine on monosodium urate crystal-induced IL-1β and IL-6 release from mouse macrophages Fig.7. The effect of bucillamine and colchicine in inhibiting monosodium urate crystal-induced IL-1β release from mouse macrophages

USE OF BUCILLAMINE IN THE TREATMENT OF GOUT

CROSS-REFERENCE TO RELATED APPLICATIONS

This application is a Continuation-In-Part of U.S. application Ser. No. 14/443,639, filed May 18, 2015, which is the National Stage entry under 35 U.S.C. §371 of International Application No. PCT/CA2013/050882, filed Nov. 19, 2013, which claims the benefit of priority of Australian Application No. 2012905072, filed Nov. 20, 2012. The foregoing applications are incorporated herein by reference in their entirety.

TECHNICAL FIELD

The present invention relates to pharmaceutical compositions comprising bucillamine and their use for the treatment of gout.

BACKGROUND OF THE INVENTION

It is estimated that 8.3 million people suffer from active gout in the U.S.[1] The incidence and prevalence of gout is rising. This is due to factors such as an increase in the aged population, many of whom take thiazide diuretics and prophylactic aspirin that promote hyperuricaemia and lifestyle factors characterized by diets that include excessive fructose and alcohol intake, physical inactivity and abdominal fat accumulation which favor hyperuricaemia.[2,3]

The impaired renal excretion of uric acid is the dominant cause of hyperuricaemia in the majority of patients with gout.[4] The existence of genetic variants within a transport gene, SLC2A9, have been reported that explain 1.7% to 5.3% of the variance in serum urate concentrations in a Croatian population sample.[5] SLC2A9 variants have also been associated with a low fractional excretion of urate and the presence of gout in several other European population samples.[6] The SLC2A9 gene is found on human chromosome 4 and encodes the facilitative glucose transporter 9 (Glut9), which is a unique hexose and high-capacity urate transporter.[7] It has been shown that Glut9 is expressed in the basolateral membrane of hepatocytes and in both apical and basolateral membranes of the distal nephron in the mouse.[8] Glut9 sustains urate reabsorption in the kidney independently of the other known urate transporters URAT1, OAT1, and OAT3.[8]

It has been found recently that human ATP-binding cassette, subfamily G, member 2 (ABCG2), encoded by the ABCG2 gene, is located in the brush border membrane of kidney proximal tubule cells, where it mediates renal urate secretion.[9] Introduction of a mutation encoded by a common ABCG2 SNP (rs2231142) in *Xenopus* oocytes resulted in a 53% reduction in urate transport rates compared with wild-type ABCG2. The data obtained in a population-based study of 14,783 individuals support rs2231142 as the causal variant in the region, exhibiting highly significant associations with urate concentration. These findings suggest that this SNP has a significant pathogenic role in at least 10% of all gout cases in white persons.[9] It has been confirmed in a study in Japanese patients that common nonfunctional mutations of ABCG2 are involved in the pathology of gout.[10]

The risk of developing gout is related to the degree of hyperuricaemia[11,12] and increases rapidly after the serum urate concentration exceeds ~400 µmol/L which is close to the level at which monosodium urate (MSU) crystals precipitate out of serum in vitro.[13] It has been established that phagocytosed intracellular MSU crystals are detected in the cytoplasm by the NALP3 inflammasome in monocytes or macrophages.[14] The result is activation of caspase-1, which initiates IL-1β maturation and secretion. In turn, interleukin IL-1β secretion produces various pro-inflammatory mediators, which elicit neutrophil influx into the joints.[14] The results of in-vivo studies have confirmed that IL-1β and its pathway is crucially associated with the inflammatory response induced by MSU crystals, suggesting that IL-1β is a pivotal mediator of inflammation in acute gout as well as chronic gout and a key therapeutic target.[15,16]

The first-line urate-lowering therapy for the treatment of gout over the past four decades has been allopurinol which lowers serum urate levels by the inhibition of xanthine oxidase.[17] The FDA guidelines recommend increasing the dose progressively from an initial dose of 100 mg a day to a maximum of 800 mg a day until the target serum urate (SU) level of ≤6 mg/dL ((≠357 µmol/L) is achieved.[18] However, the vast majority of allopurinol prescriptions are for doses of 300 mg a day or less. This situation has been promoted by the persistence of longstanding non-evidence based dosing guidelines that were originally designed to avoid the allopurinol hypersensitivity syndrome without any consideration for efficacy.[18]

Febuxostat (Ulloric®, Takeda) is a urate lowering therapy recently approved by the FDA for the treatment of chronic gout. It is a non-purine-analogue inhibitor of xanthine oxidase that lowers circulating uric acid levels.[17] It was found that febuxostat was more effective than allopurinol in attaining appropriate SU levels (<360 µmol/L), but 59% of patients who previously failed to normalise uric acid levels <360 µmol/L) on allopurinol also failed on febuxostat 80 mg/day.[19] Febuxostat is an alternative for patients for whom allopurinol is relatively contraindicated, due to a lack of evidence-based studies, particularly in mild to moderate renal dysfunction where dose modification is not required. The main side effects of febuxostat include raised hepatic enzymes and a small increase in the rate of serious cardiovascular events which preclude its use in ischaemic or congestive heart failure.

The ageing of the population and the proliferation of unhealthy lifestyles together with the sub-optimal use of allopurinol and uncertainty concerning the place of febuxostat emphasises the need for new drugs for the treatment of gout.

The present inventor has realised that the recent advances in the molecular genetics of renal urate transporters together with the discovery of the inflammasome may offer the opportunity to develop novel therapeutic agents based on the identification of specific targets that are involved in the pathology of gout.

Bucillamine, (Rimatil®, N-(2-mercapto-2-methylpropionyl)-L-cysteine) is manufactured by Santen Pharmaceutical Co. Ltd. It is a disease-modifying anti-rheumatic drug which is used as a first-line treatment for rheumatoid arthritis in Japan.[20] Bucillamine is a member of a group of low molecular weight, cysteine-derived thiol donors that includes N-acetylcysteine and N-2-mercaptopropionyl glycine.[21,22] These compounds readily enter cells through the cysteine transport pathway and exert their antioxidant effect by maintaining the endogenous glutaredoxin (Gtx) and thioredoxin (TRx) systems in a reduced state by transfer of thiol groups.[21,22] Bucillamine contains two donatable thiol groups, making it a considerably more potent antioxidant than N-acetylcysteine or N-2-mercaptopropionyl glycine which each contain only one thiol group.[23-25] The present inventor has appreciated that in addition to its direct antioxidant action, bucillamine also increases the transcriptional activity of Nrf2.[26]

Structure of Bucillamine

The physiological importance of ABCG2 in humans is illustrated by the large differences in SU levels and the prevalence of gout caused by genetic variation in ABCG2. It is therefore, a potential target for new uricosuric agents in the treatment of gout.[9, 10] It has been shown that ABCG2 (BCRP) is induced by the Nrf2 activators olitpraz in primary human hepatocytes[27] and tert-butylhydroquinone in HepG2 cells.[28]

The multidrug resistance protein 4 (MRP4/ABCC4) has been identified as a unidirectional efflux pump for urate with multiple allosteric substrate binding sites located at the apical membrane of kidney proximal tubules.[29] The treatment of wild-type and Nrf2-null mice with oltipraz and butylated hydroxyanisole demonstrated that the induction of ABCC4 was Nrf2-dependent.[30] Oltipraz also induces ABCC4 (MRP4) mRNA and protein expression in HepG2 cells and primary human hepatocytes via the Nrf2 transcription pathway.[31]

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

SUMMARY OF THE INVENTION

The present inventor hypothesized that bucillamine could have similar effects as oltipraz on ABCC4.

The Nrf2-dependent induction of renal MRP4 (ABCC4) protein has observed in cisplatin-treated wild-type mice.[32] The present inventor hypothesized that renal ABCC4 may be upregulated by Nrf2 activating compounds such as olitipraz or bucillamine.

The xanthine oxidase inhibitor allopurinol and its active metabolite oxypurinol have both been shown to stimulate MRP4 (ABCC4) mediated urate transport suggesting a new mechanism that may contribute to their urate lowering effect.[33] The present inventor hypothesized that the use of a combination of allopurinol and an Nrf2 activator such as bucillamine has a synergistic effect in lowering the SU.

It has been reported previously that fenofibrate has a rapid urate-lowering effect in patients with hyperuricaemia and gout being treated with allopurinol.[34] Fenofibrate increases renal uric acid clearance but the exact mechanism has not been determined.[34, 35] One possibility is that it may induce urate transporters through the activation of Nrf2.[36] Moreover, a number of studies have reported that coffee consumption (greater than 5 cups of coffee) is associated with lower concentrations of urate[36, 37] and a decreased risk of gout.[38] There is evidence that coffee activates Nrf2[39, 40] which suggest that it may increase urate excretion through the activation of renal urate transporters.

The prevalence of the metabolic syndrome is high in patients with gout.[41, 42] It has been found that uric acid excretion is lower in gout patients with the metabolic syndrome.[43] Moreover, this disturbance appears to be related to the severity of the metabolic syndrome.[43] The activation of Nrf2 by oltipraz decreases insulin resistance and obesity which are both elements of the metabolic syndrome.[44] In another study, the oleanolic triterpenoid CDDO-im, which is a particularly potent Nrf2 activator, prevented the development of obesity.[45] The present inventor has realised that bucillamine and other activators of Nrf2 may increase urate excretion through the attenuation of the metabolic syndrome.

It has been shown recently that uric acid triggers the association of NALP3 with thioredoxin-interacting protein (TxNIP) in a reactive oxygen radical-dependent manner.[46] In unstimulated cells, TxNIP is constitutively bound to and inhibited by thioredoxin (Trx). Following an increase in oxidative stress, this complex dissociates and TxNIP binds to NALP3 promoting the assembly and oligomerisation of the inflammasome. In support of such an activation mechanism, the knockdown of thioredoxin potentiates inflammasome activation.[46]

In particular, metabolic syndrome is defined as a clustering of at least three of five of the following medical conditions: abdominal (central) obesity, elevated blood pressure, elevated fasting plasma glucose, high serum triglycerides, and low high-density lipoprotein (HDL) levels. Metabolic syndrome is associated with the risk of developing cardiovascular disease and diabetes. Some studies have shown the prevalence in the USA to be an estimated 34% of the adult population, and the prevalence increases with age. Metabolic syndrome is also known as metabolic syndrome X, cardiometabolic syndrome, syndrome X, insulin resistance syndrome, Reaven's syndrome (named for Gerald Reaven), and CHAOS (in Australia).

In work on the present invention, the inventor has appreciated that Bucillamine may attenuate the activation of NALP3 by MSU crystals. Without being bound to any particular theory, it could act through the direct transfer of thiol groups to Trx.[21, 22] In addition bucillamine can activate Nrf2[26] and the binding of the transcription factor Nrf2 to the ARE of the Trx gene is an induction mechanism for thioredoxin.[47]

The FDA recently approved colchicine (Colcrys™, URL Pharma) for the prophylaxis of acute gout flares.[48] Colchicine has been used for many years as an unapproved drug with no FDA-approved prescribing information, dosage recommendations, or drug interaction warnings. Colchicine targets the initial stage of inflammation in gout[49] but acts upstream of the inflammasome.[50] The inventor has realized that bucillamine and colchicine has a synergistic effect in attenuating inflammation during acute gout flares.

In work on the present invention, the inventor surprisingly found for the first time, that bucillamine has a potent uricosuric effect. Particularly when used in conjunction with allopurinol, bucillamine provides a promising combination for the treatment of gout. Moreover, bucillamine has potent anti-inflammatory effects that may be particularly useful in the management of acute gout flares. In addition, the inventor found that bucillamine together with colchicine produced a synergistic effect, which may offer a new combination therapy for gout with increased efficacy and fewer side effects than with colchicine alone.

Accordingly, in a first aspect of the invention there is provided, a pharmaceutical composition comprising bucillamine or a pharmaceutically acceptable salt or solvate thereof, together with one or more pharmaceutically acceptable carriers, diluents and excipients.

Accordingly, in a second aspect of the invention there is provided, a pharmaceutical composition comprising bucillamine or a pharmaceutically acceptable salt or solvate thereof and allopurinol or a pharmaceutically acceptable salt or solvate thereof, together with one or more pharmaceutically acceptable carriers, diluents and excipients.

According to a third aspect of the invention there is provided, a pharmaceutical composition comprising bucillamine or a pharmaceutically acceptable salt or solvate thereof and colchicine or a pharmaceutically acceptable salt or solvate thereof, together with one or more pharmaceutically acceptable carriers, diluents and excipients.

According to a fourth aspect of the invention there is provided, a method for the treatment of gout in a mammal comprising administering a therapeutically effective amount of bucillamine or a pharmaceutically acceptable salt or solvate thereof and allopurinol or a pharmaceutically acceptable salt or solvate thereof, to a mammal in need thereof.

According to a fifth aspect of the invention there is provided, a method for the treatment of gout in a mammal comprising administering therapeutically effective amount of bucillamine or a pharmaceutically acceptable salt or solvate thereof and colchicine or a pharmaceutically acceptable salt or solvate thereof, to a mammal in need thereof.

According to a sixth aspect of the invention there is provided, a use of bucillamine or a pharmaceutically acceptable salt or solvate thereof and allopurinol or a pharmaceutically acceptable salt or solvate thereof, in the manufacture of a medicament for the treatment of gout.

According to a seventh aspect of the invention there is provided, a use of bucillamine or a pharmaceutically acceptable salt or solvate thereof and colchicine or a pharmaceutically acceptable salt or solvate thereof, in the manufacture of a medicament for the treatment of gout.

According to a eighth aspect of the invention there is provided, a pharmaceutical composition according to the first or second aspects of the invention for use in the treatment of gout.

The present invention demonstrates, for the first time, that bucillamine has a uricosuric effect in hyperuricaemic mice that may be attributable to the enhancement of uric acid excretion. Moreover, the combination of bucillamine and allopurinol has a potent synergistic effect. Without being bound to any particular theory, one possible mechanism may be the stimulation of MRP4 (ABCC4) mediated urate transport by bucillamine and allopurinol.[30, 31, 33]

It was found that bucillamine was effective in preventing neutrophil trafficking to the peritoneum following the injection of monosodium urate crystals. The drug also attenuated the release of IL-1β and IL-6 into the peritoneal cavity. Bucillamine has been shown previously to reduce neutrophil-endothelial cell interactions in warm ischaemia—reperfusion injury in the liver.[58] The most likely mechanism of action may be through the inhibition of the cytokine-induced neutrophil chemoattractant-1 (CINC-1) which is induced by IL-1β and TNF-α and promotes both neutrophil rolling and adhesion through the upregulation of surface integrins.[58]

The inventor also found, that bucillamine and colchicine synergised on the movement of neutrophils into the peritoneum and the release of IL-1β and IL-6. The mechanism of action of colchicine is thought to be partly due to its direct interaction with microtubules thereby inhibiting their migration toward the chemotactic factors.[59] Colchicine also changes the distribution of adhesion molecules on neutrophils and endothelial cells, limiting the inflammatory response in acute gout.[60] This mechanism may be complementary to bucillamine which is believed to attenuate neutrophil-endothelial cell interactions indirectly through the inhibition of CINC-1.[58]

In preliminary experiments, it was found that bucillamine inhibited the release of IL-1β and IL-6 from mouse macrophages in response to MSU crystals. It has been shown previously that bucillamine attenuated the release of TNF-α, IL-1β and IL-8 from THP-1 cells stimulated with lipopolysaccharide.[61] This suggests that bucillamine may be an inhibitor of MSU crystal-induced inflammasome activation. It has been demonstrated that the processing of IL-1β is the central event in the inflammatory cascade initiated by MSU crystals.[50]

Bucillamine had an additive effect with colchicine on the release of IL-1β from mouse macrophages following exposure to monosodium urate crystals. Colchicine has been shown to block crystal-induced IL-1β generation at the level of crystal endocytosis and presentation to the inflammasome.[50]

Colchicine has the narrowest therapeutic window of any acute gout therapy and there is a considerable variability in tolerance between patients.[62, 63] However, it has been shown recently that lower doses retain efficacy with reduced toxicity in the treatment of acute gout attacks.[62] Colchicine has been the mainstay of treatment for gout prolphylaxis. The use of a combination of bucillamine with colchicine could further improve the therapeutic profile of colchicine as a prophylaxis treatment especially when given chronically in order to prevent gout attacks.

DESCRIPTION OF THE PREFERRED EMBODIMENTS OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

For use in therapy a therapeutically effective amount of the bucillamine and allopurinol or colchicine as defined herein, or pharmaceutically acceptable salts or solvates thereof, may be presented as a pharmaceutical composition. Thus, in a further embodiment the invention provides a pharmaceutical composition according to the first, and second aspects, in admixture with one or more pharmaceutically acceptable carriers, diluents, or excipients. The carrier(s), diluent(s) or excipient(s) must be acceptable in the sense of being compatible with the other ingredients of the formulation and not deleterious to the recipient thereof.

When applicable, the compositions of the present invention, including bucillamine and allopurinol or colchicine may be in the form of and/or may be administered as a pharmaceutically acceptable salt.

Typically, a pharmaceutically acceptable salt may be readily prepared by using a desired acid or base as appropriate. The salt may precipitate from solution and be collected by filtration or may be recovered by evaporation of the solvent.

Suitable addition salts are formed from acids which form non-toxic salts and examples are hydrochloride, hydrobromide, hydroiodide, sulphate, nitrate, phosphate, hydrogen phosphate, dihydrogen phosphate acetate, maleate, malate, fumarate, lactate, tartrate, citrate, formate, gluconate, succinate, pyruvate, oxalate, oxaloacetate, trifluoroacetate, saccharinate, benzoate, methanesulphonate, ethanesulphonate, benzenesulphonate, p-toluenesulphonate and isethionate.

Suitable salts may also be formed from bases, forming salts including ammonium salts, alkali metal salts such as those of sodium and potassium, alkaline earth metal salts such as those of calcium and magnesium.

Pharmaceutically acceptable salts may also be prepared from other salts, including other pharmaceutically acceptable salts, using conventional methods.

Those skilled in the art of organic or coordination chemistry will appreciate that many organic and coordination compounds can form complexes with solvents in which they are reacted or from which they are precipitated or crystallized. These complexes are known as "solvates". For example, a complex with water is known as a "hydrate". Solvates of bucillamine, allopurinol and/or colchicine are within the scope of the present invention.

Pharmaceutical compositions of the invention may be formulated for administration by any appropriate route, for example by the oral (including buccal or sublingual). Therefore, the pharmaceutical compositions of the invention may be formulated, for example, as tablets, capsules, powders, granules, lozenges, creams or liquid preparations, such as oral solutions or suspensions. Such pharmaceutical formulations may be prepared by any method known in the art of pharmacy, for example by bringing into association the active ingredient with the carrier(s) or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan, monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

It should be understood that in addition to the ingredients particularly mentioned above, the formulations may include other agents conventional in the art having regard to the type of formulation in question.

The compositions of the present invention may be suitable for the treatment of diseases in a human or animal patient. In one embodiment, the patient is a mammal including a human, horse, dog, cat, sheep, cow, or primate. In one embodiment the patient is a human. In a further embodiment, the patient is not a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition of the invention. The term treatment encompasses the use in a palliative setting According to one embodiment of the invention, a pharmaceutical composition according to the first or second aspect is used in the treatment of gout. In one embodiment the gout is moderate to severe gout. In another embodiment the gout is chronic gout. In yet another embodiment the gout is acute gout.

According to another embodiment of the first or second aspects of the invention, the pharmaceutical composition comprises between 25 mg, and 400 mg of bucillamine or a pharmaceutically acceptable salt or solvate thereof. Preferably, the said composition comprises between 50 mg, and 300 mg of bucillamine or a pharmaceutically acceptable salt or solvate thereof. Most preferably, the said composition comprises between 50 mg, and 200 mg of bucillamine or a pharmaceutically acceptable salt or solvate thereof.

According to another embodiment, the pharmaceutical composition comprises between 25 mg and 8,000 mg of bucillamine or a pharmaceutically acceptable salt or solvate thereof. Preferably, the composition comprises between 400 mg and 4000 mg of bucillamine or a pharmaceutically acceptable salt or solvate thereof. More preferably, the composition comprises between 800 mg and 4000 mg of bucillamine or a pharmaceutically acceptable salt or solvate thereof. Most preferably, the composition comprises between 800 mg and 2000 mg of bucillamine or a pharmaceutically acceptable salt or solvate thereof, for example, 1800 mg thereof. According to another embodiment, the pharmaceutical composition of bucillamine or a pharmaceutically acceptable salt or solvate thereof is for administration daily, every second day, every third day, or weekly.

In another embodiment, according to the first aspect of the invention, the pharmaceutical composition comprises between 200 mg and 800 mg of allopurinol or a pharmaceutically acceptable salt or solvate thereof. Preferably, the said composition comprises between 300 mg and 600 mg of allopurinol or a pharmaceutically acceptable salt or solvate thereof. Most preferably, the said composition comprises between 300 mg and 400 mg of allopurinol or a pharmaceutically acceptable salt or solvate thereof.

In yet another embodiment, according to the second aspect of the invention, the pharmaceutical composition comprises between 0.2 mg and 1.8 mg of colchicine or a pharmaceutically acceptable salt or solvate thereof. Preferably, the said composition comprises between 0.2 mg and 1.6 mg of colchicine or a pharmaceutically acceptable salt or solvate thereof. Most preferably, the said composition comprises between 0.3 mg and 1.2 mg of colchicine or a pharmaceutically acceptable salt or solvate thereof.

In a preferred embodiment of the invention, according to the third or fourth aspects, the bucillamine and allopurinol or colchicine, or pharmaceutically acceptable salts or solvates thereof are administered concurrently as a single dose once a day. In another preferred embodiment, the bucillamine and allopurinol or colchicine, or pharmaceutically acceptable salts or solvates thereof are administered orally.

According to another embodiment of the third or fourth aspects of the invention, the said method comprises administering between 25 mg, and 400 mg of bucillamine or a pharmaceutically acceptable salt or solvate thereof. Preferably, the said method comprises administering between 50 mg and 300 mg of bucillamine or a pharmaceutically acceptable salt or solvate thereof. Most preferably, the said method comprises administering between 50 mg, and 200 mg of bucillamine or a pharmaceutically acceptable salt or solvate thereof.

In another embodiment according to the third aspect of the invention, the said method comprises administering between 200 mg and 800 mg of allopurinol or a pharmaceutically acceptable salt or solvate thereof. Preferably, the said method comprises administering between 300 mg and 600 mg of allopurinol or a pharmaceutically acceptable salt or solvate thereof. Most preferably, the said method comprises administering between 300 mg and 400 mg of allopurinol or a pharmaceutically acceptable salt or solvate thereof.

In yet another embodiment, according to the fourth aspect of the invention, the said method comprises administering between 0.2 mg and 1.8 mg of colchicine or a pharmaceutically acceptable salt or solvate thereof. Preferably, the said method comprises administering between 0.2 mg and 1.6 mg of colchicine or a pharmaceutically acceptable salt or solvate thereof. Most preferably, the said method comprises administering between 0.3 mg and 1.2 mg of colchicine or a pharmaceutically acceptable salt or solvate thereof.

MODES FOR CARRYING OUT THE INVENTION

In order to better understand the nature of the invention a number of examples will now be described as follows:

Example 1—Methods

Hyperuricaemic Mice and Drug Administration
Male C57/BL/6 mice were maintained on a 12-h light/dark cycle in a temperature- and humidity-controlled room for 1 week prior to the experiments. A total of 45 C57/Black 6 mice in 9 groups (n=5) were studied for a period of one week. The drugs were dissolved or dispersed in distilled water immediately prior to dosing and administered in a volume of 15 mL/kg by gastric gavage. The volume of drug administered was based on the body weight determined on the day of dosing. In order to produce hyperuricaemia, the mice received 250 mg/kg of potassium oxonate or water (vehicle) at 8.00 a.m. daily for seven consecutive days.[51-53] Treatment with bucillamine, allopurinol or vehicle was initiated one hour after the administration of potassium oxonate and continued for 7 days.

Blood and Urine Collection
Whole blood and urine samples were collected 1 h after final drug administration on the seventh day. The blood was allowed to clot for approximately 1 h at room temperature and then centrifuged at 10,000×g for 5 min to obtain the serum. The serum and urine were stored at −80° C. until assayed.

Determination of Uric Acid Levels
The uric acid levels in serum and urine were determined by the phosphotungstic acid method.[54]

Determination of Serum Creatinine Levels
The creatinine levels in serum were determined spectrophotometrically using standard diagnostic kits.

Western Blot Analysis of ABCG2 in Mouse Kidney Protein
The protein samples were prepared from mouse kidney tissues using an extraction buffer containing 50 mM Tris-HCl, pH 7.4, 0.5% SDS and protease inhibitor cocktail P8340 (Sigma), and Western blots were performed. The proteins (40 μg) from each sample were separated on a 10% SDS polyacrylamide gel (SDS-PAGE) and resolved at 180 volts for 1 h. The proteins were transferred to a strip of nitrocellulose membrane. and the ABCG2 protein was immunodetected by a 1:200 dilution of a primary mouse monoclonal anti-human ABCG2 antibody (Santa Cruz Biotechnology) or a 1:1000 dilution of a primary mouse monoclonal anti-human BCRP (BXP-21) antibody followed by a 1:3000 dilution of a secondary donkey anti-mouse IgG-HRP antibody (Santa Cruz Biotechnology). Then ECL Plus reagents (Amersham Biosciences) were applied to the blots which were then exposed to autoradiography films (Kodak) for 3 min.

Monosodium Urate Crystal-Induced Inflammation in Mice
Monosodium urate (MSU) crystals were prepared by dissolving 1.68 g of uric acid in 500 mL of 0.01 M NaOH and heating to 70° C.[55, 56] NaOH was added as required to maintain the pH between 7.1 and 7.2 and the solution was filtered and incubated at room temperature with slow stirring for 24 hours.

Male C57/BL/6 mice were treated intraperitoneally with 0.5 mg MSU crystals in 0.5 mL of sterile PBS or PBS alone as a control.[50] Bucillamine was dissolved in PBS and administered as a 50 μL i.p. injection to three groups of mice at a dose of 5, 10 or 25 μmol/kg immediately following MSU crystal injection. Colchicine was dissolved in PBS and administered at a dose of 0.05, 0.5 and 5 μmol/kg in a similar fashion. Colchicine was administered immediately following bucillamine in studies on the synergistic effects of the two drugs. The mice were euthanised after 6 hours with $CO_2$ and the peritoneal cells removed by lavage with 10 mL of cold PBS. The lavage fluid was analysed for neutrophil infiltration using a cytospin and Diff-Quick staining. The concentrations of IL-1β and IL-6 in the lavage supernatants was determined using an R&D Systems Quantikine mouse immunoassay.

Mouse Peritoneal Macrophages

Male C57/BL/6 mice were injected intraperitoneally with 4% thioglycollate solution and the macrophages collected by peritoneal lavage 3 days later.[57] The cells were plated at a density of 7×10$^5$ cells in 12-well dishes and non-adherent cells were removed after 3 hours. The cells were cultured in RPMI containing 10% FCS, sodium pyruvate, penicillin/streptomycin and L-glutamine. The culture medium was replaced with OptiMEM and the macrophages stimulated with 50 μg/mL of MSU crystals for 6 hours in the presence or absence of bucillamine. The concentration of IL-1β in the supernatant was determined with an R&D systems Quantikine mouse immunoassay.

Results

Figure 1:
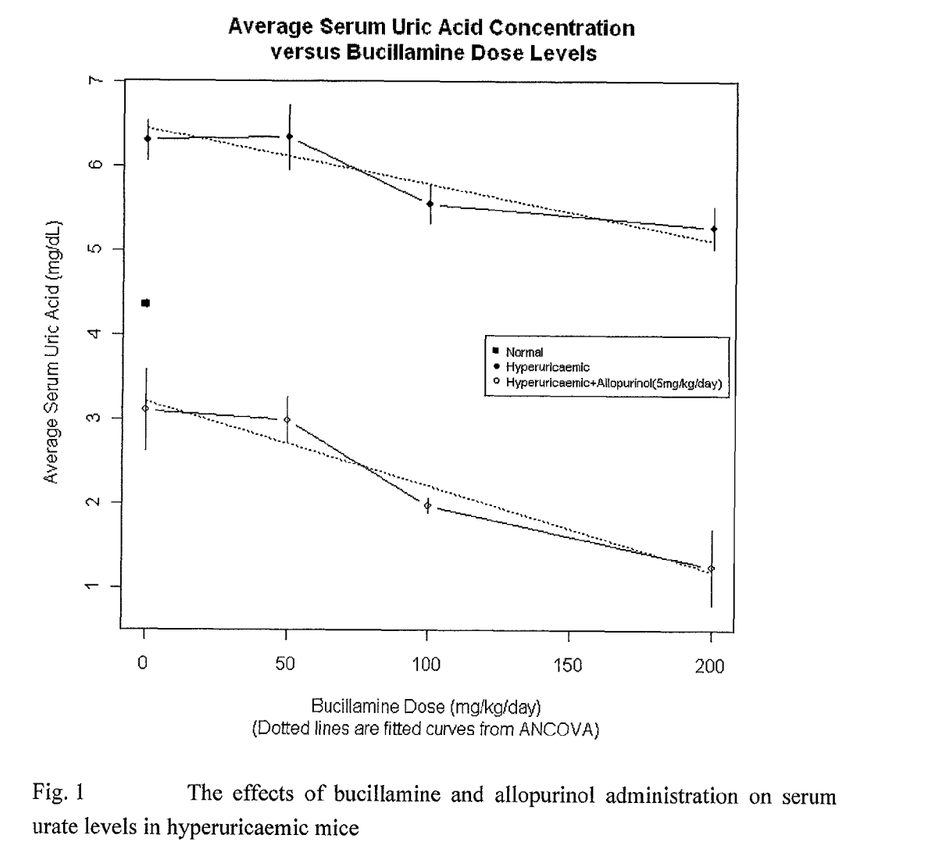
FIG. 1 shows the effects of bucillamine and allopurinol administration on serum urate levels in hyperuricaemic mice.

The Effects of Bucillamine and Allopurinol on Serum and Urinary Levels of Uric Acid and Urinary Levels of Creatinine in Hyperuricaemic and Normal Mice The effects of bucillamine and allopurinol administration on serum urate levels in hyperuricaemic mice are shown in FIG. 1. Bucillamine had a highly significant ($p<0.001$) dose-response effect which reduced mean serum urate by 0.0067 mg/dL for each increase of 1 mg/kg/day. The administration of allopurinol (5 mg/kg/day)) produced a highly significant ($p<0.001$) drop in serum urate, to a level significantly below normal baseline ($p<0.001$). There was a significant ($p=0.012$) interactive effect between bucillamine and allopurinol. The addition of allopurinol (5 mg/kg/day)) increased the dose-response effect of bucillamine so that each increase of 1 mg/kg/day of bucillamine resulted in a decrease of 0.0010 mg/dL in the serum urate concentration.

Figure 2:
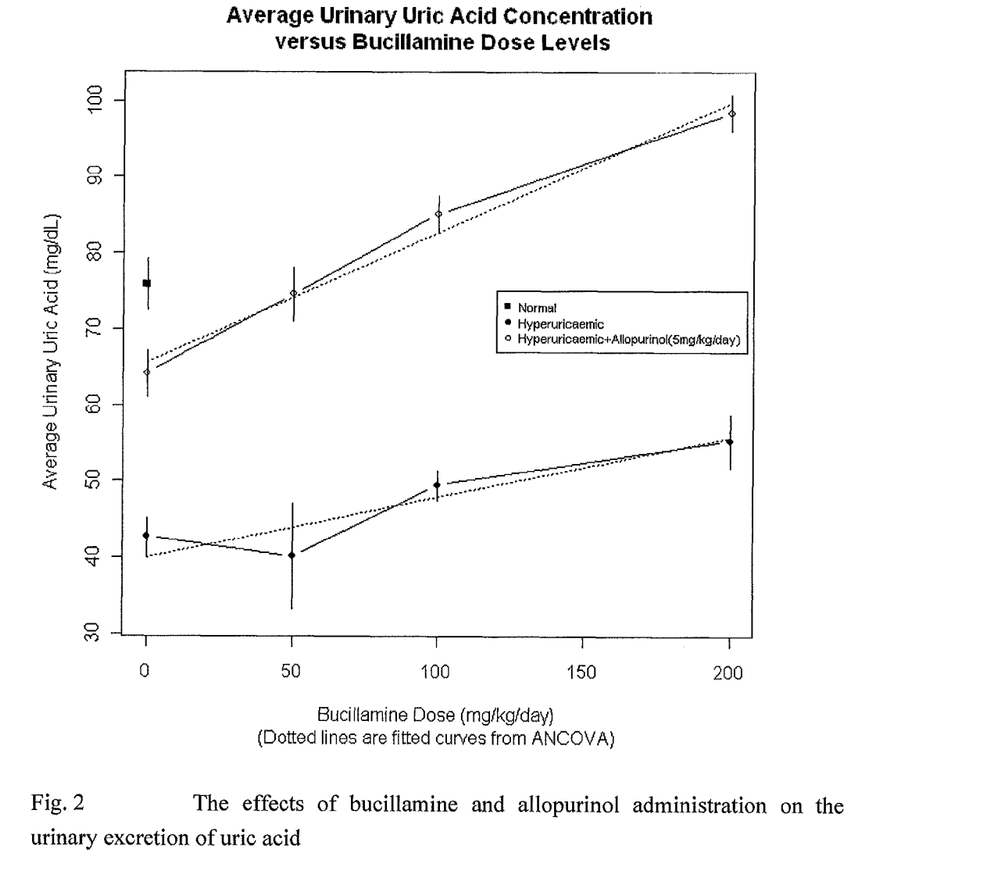
FIG. 2 shows the effects of bucillamine and allopurinol administration on the urinary excretion of uric acid.

FIG. 2 shows the effects of bucillamine and allopurinol administration on the urinary excretion of uric acid. Bucillamine had a highly significant ($p<0.001$) dose-response effect which increased mean urinary uric acid by 0.079 mg/dL for each increase of 1 mg/kg/day of the drug. Allopurinol (5 mg/kg/day) produced a highly significant ($p<0.001$) increase in urinary uric acid. to a level still significantly below normal baseline ($p<0.001$). There was a highly significant ($p<0.001$) interactive effect between allopurinol and bucillamine. The addition of allopurinol (5 mg/kg/day) increased the dose-response effect of bucillamine such that each increase of 1 mg/kg/day of bucillamine resulted in an increase of 0.171 mg/dL in the urinary uric acid concentration.

Figure 3:
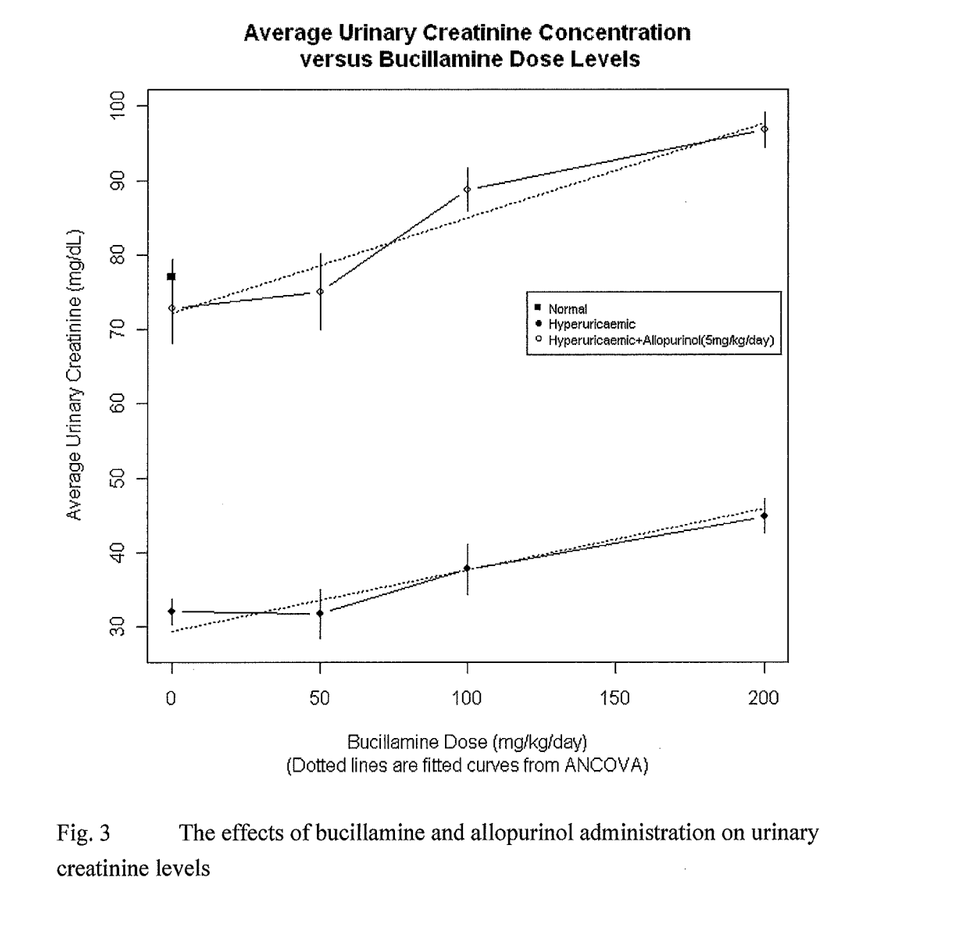
FIG. 3 shows the effects of bucillamine and allopurinol administration on urinary creatinine levels.

The results in FIG. 3 show the effects of bucillamine and allopurinol administration on urinary creatinine levels. Bucillamine had a highly significant ($p<0.001$) dose-response effect which increased mean urinary creatinine by 0.082 mg/dL for each increase of 1 mg/kg/day. There was a highly significant ($p=0.004$) interactive effect between allopurinol and bucillamine. The addition of allopurinol (5 mg/kg/day) increased the dose-response effect of bucillamine such that each increase of 1 mg/kg/day of bucillamine resulted in an increase of 0.128 mg/dL in the serum urate concentration.

The Effect of the Administration of Bucillamine on the Induction of ABCG2 in the Mouse Kidney The Western blot analysis demonstrated that ABCG2 protein was unregulated in the mouse kidney following treatment with a 100 mg/kg/day of bucillamine for 7 days (data not shown). The upregulation of ABCG2 in the presence of bucillamine may be due to the activation of Nrf2 in the kidney.[30, 31, 32]

Figure 4:
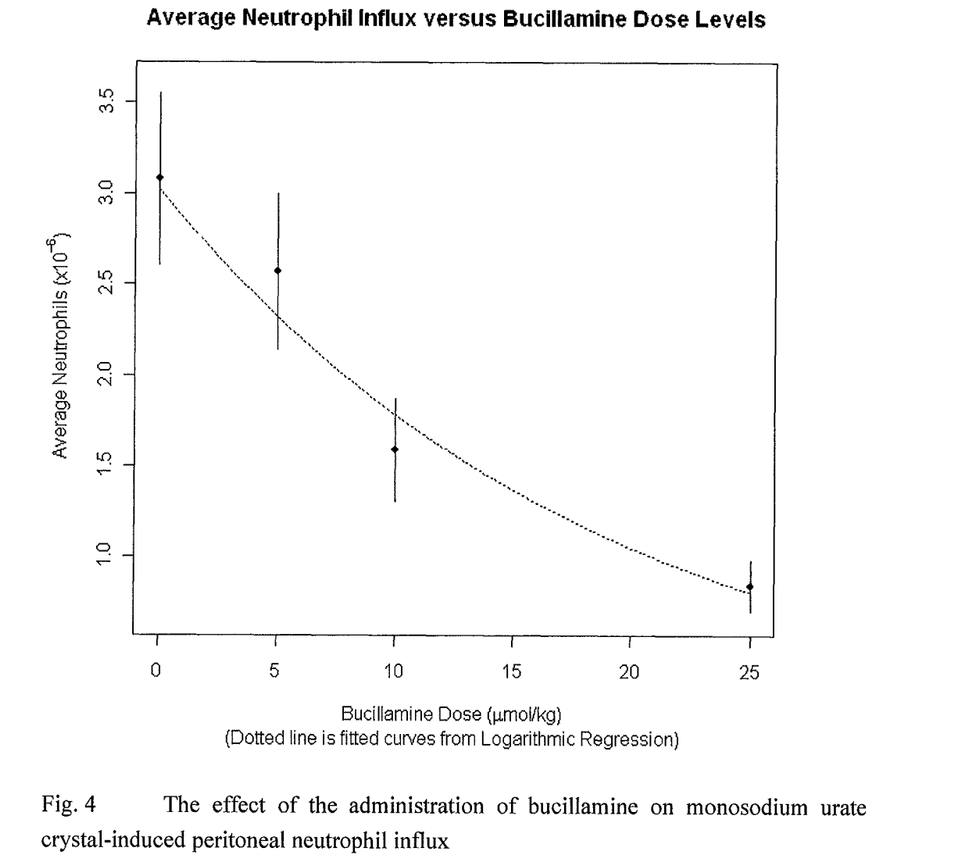
FIG. 4 shows the effect of the administration of bucillamine on monosodium urate-induced peritoneal neutrophil influx in the mouse.

The Effect of the Administration of Bucillamine on Monosodium Urate-Induced Peritoneal Inflammation in the Mouse The effect of the administration of bucillamine on monosodium urate-induced peritoneal neutrophil influx in the mouse is shown in FIG. 4. Bucillamine had a highly significant ($p<0.001$) dose-response effect which decreased mean neutrophil influx by 5.15% for every increase of 1 μmol/kg of the drug. A logarithmic model, leading to percentage decrease estimates, was chosen after examining the residual plot from a standard linear regression, which clearly displayed both curvature and heteroskedasticity. These issues were both solved by the logarithmic transformation applied to the neutrophil values.

Figure 5:
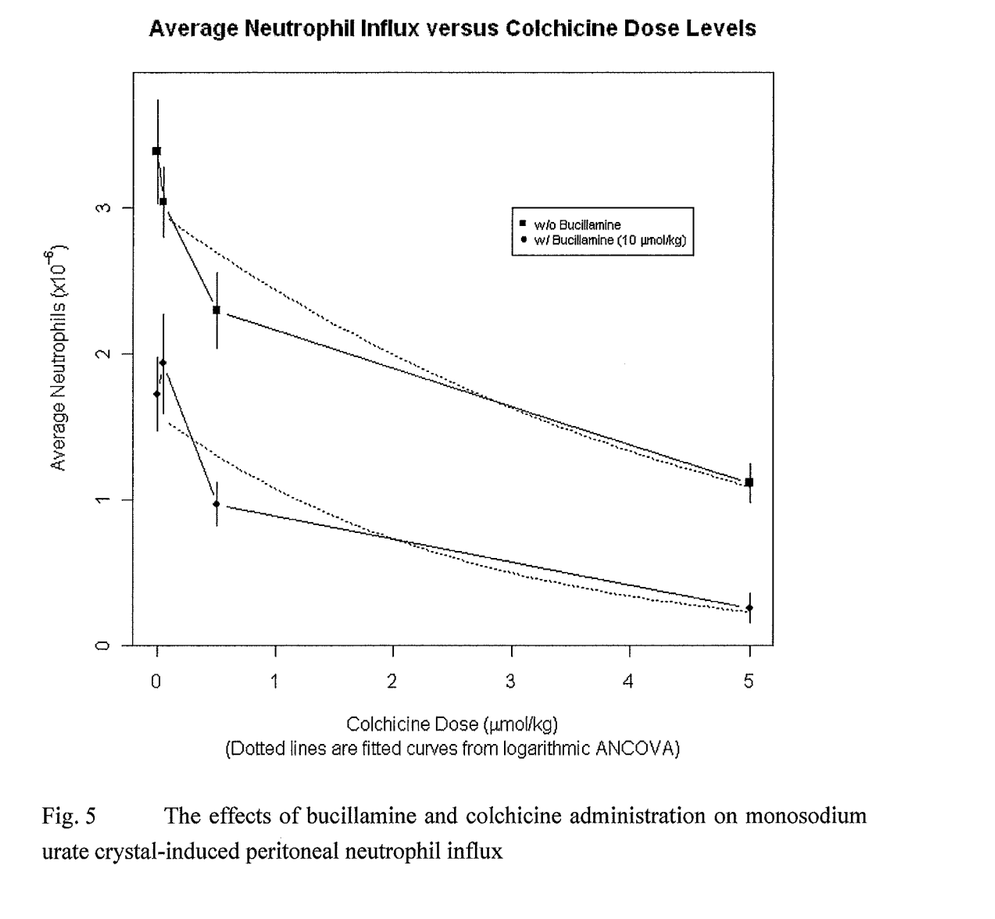
FIG. 5 shows the effects of bucillamine and colchicine administration on MSU crystal-induced peritoneal neutrophil influx in the mouse.

The Effects of the Administration of Bucillamine and Colchicine on Monosodium Urate-Induced Peritoneal Inflammation in the Mouse FIG. 5 shows the effects of bucillamine and colchicine administration on MSU crystal-induced peritoneal neutrophil influx in the mouse. Colchicine had a highly significant ($p<0.001$) dose-response effect which decreased average neutrophil influx by 18.3% for every increase of 1 μmol/kg. A logarithmic model was chosen after examining the shape of the relationship between neutrophil influx and colchicine dose. It was found that the addition of bucillamine (10 μmol/kg) produced a highly significant ($p<0.001$) decrease in average neutrophil influx. In addition, there was an interactive relationship between bucillamine and colchicine such that the addition of bucillamine enhanced the dose-response effect so that there was a decrease of 32.2% for every increase of 1 μmol/kg of colchicine.

Figure 6:
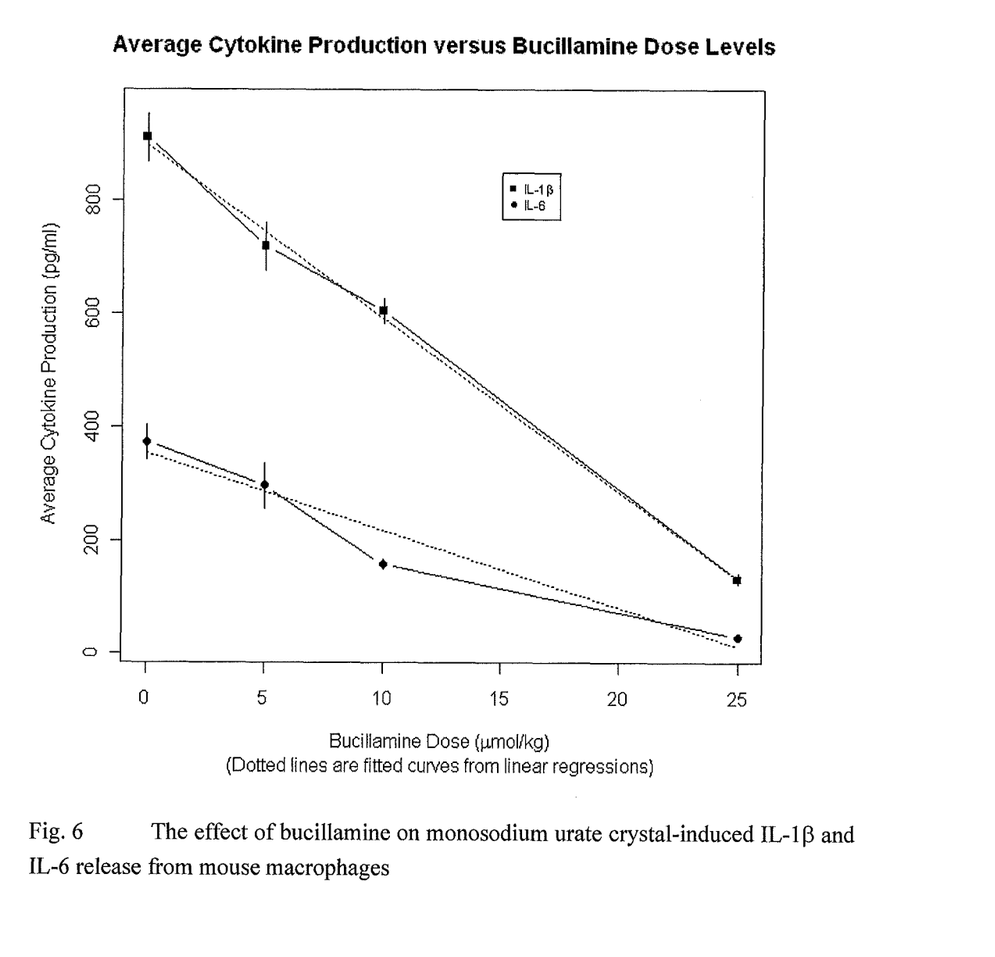
FIG. 6 shows the effect of bucillamine on MSU crystal-induced IL-1β and IL-6 release from mouse macrophages.
Figure 7:
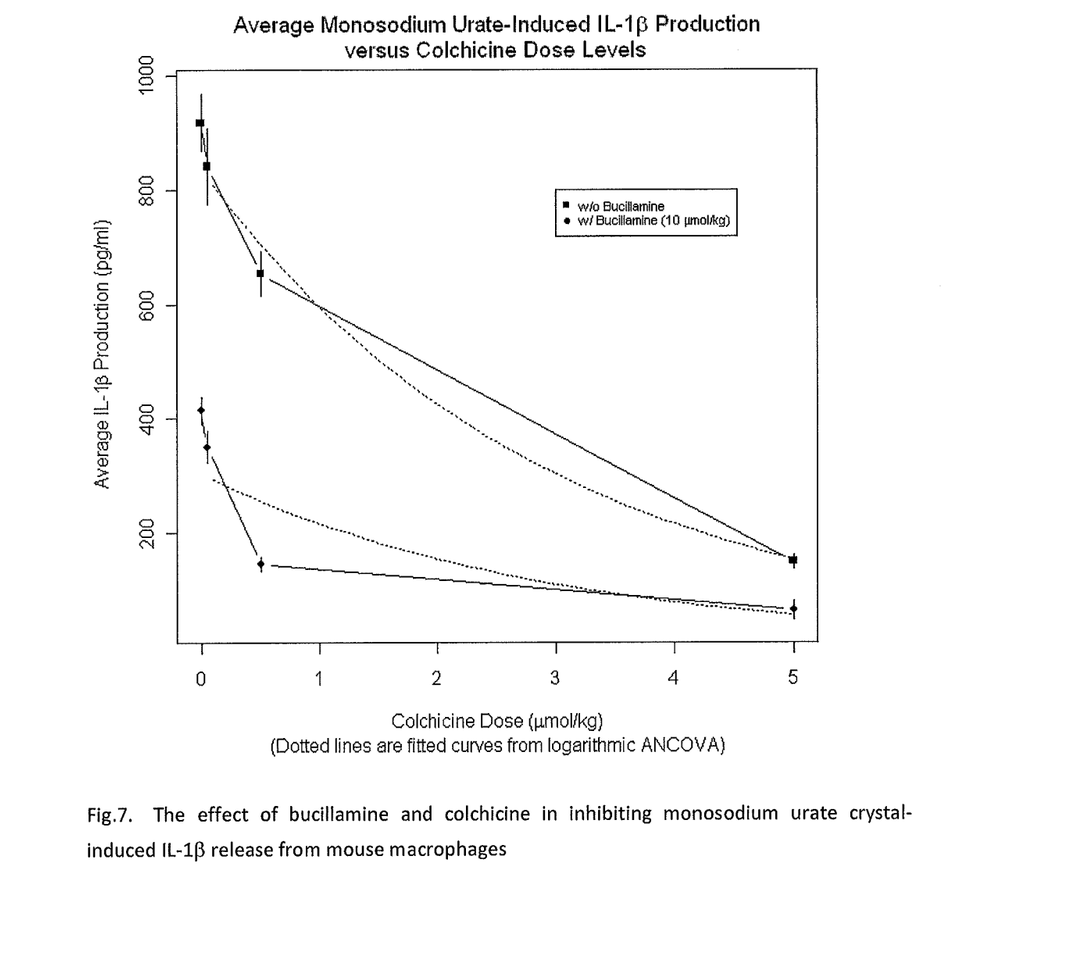
FIG. 7 shows the effect of bucillamine and colchicine in inhibiting monosodium urate crystal-induced IL-1β release from mouse macrophages

The Effects of Bucillamine on Monosodium Urate-Induced IL-1β and IL-6 Release from Mouse Macrophages The effect of bucillamine on MSU crystal-induced IL-1β and IL-6 release from mouse macrophages is shown in FIG. 6. Bucillamine has a highly significant ($p<0.001$) dose response effect on IL-1β cytokine production, with each additional 1 μmol/kg increase in bucillamine resulting in a decrease in average IL-1β cytokine production of 30.7 pg/mL. Bucillamine has a highly significant ($p<0.001$) dose response effect on IL-6 cytokine production, with each additional 1 μmol/kg increase in bucillamine resulting in a decrease in average IL-6 cytokine production of 13.7 pg/mL. However, this dose-response effect was significantly ($p<0.001$) less than the dose response effect on average IL-1β cytokine production.

The Effects of Bucillamine and Colchicine on Monosodium Urate-Induced IL-1β Release from Mouse Macrophages The effect of bucillamine and colchicine in inhibiting MSU crystal-induced IL-1β release from mouse macrophages is shown in FIG. 6. Colchicine had a highly significant ($p<0.001$) dose-response effect which decreased average MSU crystal-induced IL-1β production by 29.6% for every increase of 1 μmol/kg. A logarithmic model was chosen after examining the shape of the relationship between IL-1β production and the dose of colchicine. The addition of bucillamine (10 μmol/kg) produced a highly significant ($p<0.001$) decrease in average MSU crystal-induced IL-1β production of 65.0%. However, there was no significant interactive relationship between the dose of bucillamine and colchicine.

Example 2—Clinical

An open-label, multicenter, active-controlled, parallel-group clinical trial was designed to evaluate various doses of Bucillamine compared with Colchicine in the treatment of subjects with acute gout flares over a seven-day treatment period. At approximately 20 clinical sites in the United States, the study aimed to enroll sixty-six eligible subjects, who are confirmed with qualifying gout flare, and who are randomized in a 1:1:1 allocation ratio to either Arm A (Bucillamine—900 mg), Arm B (Bucillamine—1,800 mg) or Arm C (Colchicine—1.8 mg) over a seven-day treatment period.

The primary efficacy endpoint is the proportion of patients who responded to treatment. Treatment responders are defined as a ≥50% reduction in target joint pain score from baseline at 72 hours post-dose without using rescue drug. The target joint pain score is an 11-point Pain Intensity Numeric Rating Scale (PI-NRS) used to assess joint pain intensity while experiencing a gout flare on a scale from 0 (no pain) to 10 (worst possible pain). The PI-NRS is completed using a diary where the subject is required to circle the most appropriate number that best describe their level of pain in the identified target joint during specific time points, for example at 24 hours, 48 hours, and 72 hours post-dose.

TABLE 1

Results

| Site ID | Subject ID | Randomized | 0 hr | 24 hr | 48 hr | 72 hr | Response % |
|---|---|---|---|---|---|---|---|
| 1 | 0102 | C | 7 | 5 | 4 | 3 | 57.14% |
| 2 | 0201 | C | 7 | 4 | 3 | 0 | 100.00% |
| 3 | 0301 | C | 10 | 9.5 | 9.5 | 10 | 0.00% |
| 3 | 0302 | B | 7 | 4 | 3 | 4 | 42.86% |
| 3 | 0303 | A | 8 | 9 | 7 | 5 | 37.60% |
| 4 | 0401 | A | 7 | 9 | 9 | 9 | -28.57% |
| 4 | 0403 | C | 8 | 5 | 3 | 3 | 62.50% |
| 4 | 0404 | B | 7 | 8 | 6 | 6 | 14.29% |
| 4 | 0406 | C | 10 | 10 | 10 | 9 | 10.00% |
| 5 | 0502 | B | 8 | 1 | 0 | 0 | 100.00% |
| 5 | 0505 | A | 9 | 7 | 6 | 6 | 33.33% |
| 5 | 0508 | C | 8 | 6 | 5 | 5 | 37.50% |
| 5 | 0509 | C | 9 | 9 | 6 | 7 | 22.22% |
| 5 | 0511 | A | 9 | 7 | 6 | 6 | 33.33% |
| 5 | 0513 | B | 8 | 5 | 5 | 3 | 62.50% |
| 5 | 0514 | C | 7 | 4 | 4 | 5 | 28.57% |
| 8 | 0801 | C | 8 | 9 | 8 | 8 | 0.00% |
| 8 | 0802 | A | 10 | 9 | 9 | 9 | 10.00% |
| 8 | 0805 | B | 10 | 4 | 5 | 4 | 60.00% |
| 8 | 0806 | C | 7 | 6 | 5 | 6 | 14.29% |
| 8 | 807 | B | 10 | 7 | 6 | 5 | 50.00% |
| 13 | 1301 | B | 10 | 6 | 4 | 3 | 70.00% |
| 13 | 1302 | A | 8 | 6 | 5 | 6 | 25.00% |
| 13 | 1303 | C | 7.6 | 1 | 1 | 0 | 100.00% |
| 16 | 1601 | A | 7 | 5 | 0 | 0 | 100.00% |
| 16 | 1603 | B | 10 | 7 | 6 | 10 | 0.00% |
| 16 | 1602 | C | 10 | 0 | 0 | 0 | 100.00% |
| 16 | 1604 | A | 8 | 4 | 4 | 2 | 75.00% |
| 16 | 1605 | B | 8 | 0 | 0 | 1 | 100.00% |

The results from the study yielded the following key findings, which is based on the diaries of twenty-nine subjects:

In Arm B (Bucillamine—1,800 mg), 67% (6/9 subjects) had a ≥50% reduction in target joint pain score from baseline at 72 hours post-dose;

In Arm C (Colchicine—1.8 mg), 42% (5/12 subjects) had a ≥50% reduction in target joint pain score from baseline at 72 hours post-dose;

In Arm A (Bucillamine—900 mg), 25% (2/8 subjects) had a ≥50% reduction in target joint pain score from baseline at 72 hours post-dose;

All subjects randomized in Arm B completed the treatment period without the use of rescue medication; and No related serious adverse events were reported in any of the treatment arms.

The efficacy results, especially the response rate from Arm B in the study, demonstrate Bucillamine as a treatment of gout, including acute gout flares.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Each patent, patent application, and publication cited or described in the present application is hereby incorporated by reference in its entirety as if each individual patent, patent application, or publication was specifically and individually indicated to be incorporated by reference.

REFERENCES

1. Lawrence R. C., Felson D. T., Helmick C. G., Arnold L. M., Choi H., Deyo R. A., et al. _Estimates of the prevalence of arthritis and other rheumatic conditions in the United States. Part II. *Arthritis Rheum.* 2008; 58: 26-35.
2. Wallace K. L., Riedel A. A., Joseph-Ridge N., Wortmann R. Increasing prevalence of gout and hyperuricemia over 10 years among older adults in a managed care population. *J. Rheumatol.* 2004; 31: 1582-1587.
3. Choi H. K. A prescription for lifestyle change in patients with hyperuricemia and gout. *Curr Opin Rheumatol.* 2010; 22: 165-172.
4. Terkeltaub R., Bushinsky D. A., Becker M. A. Recent developments in our understanding of the renal basis of hyperuricemia and the development of novel antihyperuricemic therapeutics. *Arthritis Res. Ther.* 2006; 8 (Suppl: 1): S4.
5. Vitart V., Rudan I., Hayward C., Gray N. K., Floyd J., Palmer C. N., et al. SLC2A9 is a newly identified urate transporter influencing serum urate concentration, urate excretion and gout *Nature Genetics* 2008; 40: 437-442.
6. Doblado M., Moley K. H. Facilitative glucose transporter 9, a unique hexose and urate transporter. *Am. J. Physiol. Endocrinol. Metab.* 2009; 297: E831-835.
7. Phay J. E., Hussain H. B., Moley J. F. Cloning and expression analysis of a novel member of the facilitative glucose transporter family, SLC2A9 (GLUT9). *Genomics* 2000; 66: 217-220.
8. Preitner F., Bonny O., Laverrière A., Rotman S., Firsov D., Da Costa A., et al. Glut9 is a major regulator of urate homeostasis and its genetic inactivation induces hyperuricosuria and urate nephropathy. *Proc. Natl. Acad. Sci. USA.* 2009; 106: 15501-15506.
9. Woodward O. M., Köttgen A., Coresh J., Boerwinkle E., Guggino W. B., Köttgen M. et al. Identification of a urate transporter, ABCG2, with a common functional polymorphism causing gout. *Proc. Natl. Acad. Sci. USA.* 2009; 106: 10338-10342.

10. Matsuo H., Takada T., Ichida K., Nakamura T., Nakayama A., Ikebuchi Y., et al. Common defects of ABCG2, a high-capacity urate exporter, cause gout: a function-based genetic analysis in a Japanese population. *Sci. Transl. Med.* 2009; 1: 5ra11.

11. Campion E. W., Glynn R. J., DeLabry L. O. Asymptomatic hyperuricemia. Risks and consequences in the Normative Aging Study. *Am. J. Med.* 1987; 82: 421-426.

12. Agudelo C A, Wise C M. Crystal-associated arthritis. *Clin. Geriatr. Med.* 1998; 14: 495-513.

13. Loeb J. N. The influence of temperature on the solubility of monosodium urate. *Arthritis Rheum.* 1972; 15: 189-192.

14. Martinon F., Petrilli V., Mayor A., Tardivel A., Tschopp J., Gout-associated uric acid crystals activate the NALP3 inflammasome, *Nature* 2006; 440: 237-241

15. Petrilli V., Martinon F. The inflammasome, autoinflammatory diseases, and gout, *Joint Bone Spine* 2007; 74: 571-576

16. Chen C. J., Shi Y., Hearn A., Fitzgerald K., Golenbock D., Reed G., Akira S. et al., MyD88-dependent IL-1 receptor signaling is essential for gouty inflammation stimulated by monosodium urate crystals, *J. Clin. Invest.* 2006; 116: 2262-2271.

17. Richette P., Bardin T. Gout. *Lancet* 2010; 375: 318-328.

18. Chao J., Terkeltaub R. A critical reappraisal of allopurinol dosing, safety and efficacy for hyperuricemia in gout. *Curr. Rheumatol. Rep* 2009; 11: 135-1340.

19. Becker M. A., Schumacher H. R., MacDonald P. A., Lloyd E., Lademacher C. Clinical efficacy and safety of successful longterm urate lowering with febuxostat or allopurinol in subjects with gout. *J. Rheumatol.* 2009; 36: 1273-1282.

20. Nanke Y, Iwatani M, Kobashigawa T, Yago T, Yamanaka H, Kotake S. Radiographic repair in three Japanese patients with rheumatoid arthritis treated with bucillamine. *Mod. Rheumatol.* 2009; 19: 681-686.

21. Amersi F., Nelson S. K., Shen X. D., Kato H., Melinek J., Kupiec-Weglinski J. W., et al. Bucillamine, a thiol antioxidant, prevents transplantation-associated reperfusion injury. *Proc. Natl. Acad. Sci. USA.* 2002; 99: 8915-8920.

22. Whitekus M. J., Li N., Zhang M., Wang M., Horwitz M. A., Nelson S. K., et al. Thiol antioxidants inhibit the adjuvant effects of aerosolized diesel exhaust particles in a murine model for ovalbumin sensitization. *J. Immunol.* 2002; 168: 2560-2567.

23. Hiura T. S., Li N., Kaplan R., Horwitz M., Seagrave J. C., Nel A. E. The role of a mitochondrial pathway in the induction of apoptosis by chemicals extracted from diesel exhaust particles. *J. Immunol.* 2000; 165: 2703-2711.

24. Horwitz L. D., Sherman N. A. Bucillamine prevents myocardial reperfusion injury. *J. Cardiovasc. Pharmacol.* 2001; 38: 859-867.

25. Horwitz L. D. Bucillamine: a potent thiol donor with multiple clinical applications. *Cardiovasc. Drug Rev.* 2003; 21: 77-90.

26. Wielandt A. M., Vollrath V., Farias M., Chianale J. Bucillamine induces glutathione biosynthesis via activation of the transcription factor Nrf2. *Biochem. Pharmacol.* 2006; 72: 455-462.

27. Jigorel E., Le Vee M., Boursier-Neyret C., Parmentier Y., Fardel O. Differential regulation of sinusoidal and canalicular hepatic drug transporter expression by xenobiotics activating drug-sensing receptors in primary human hepatocytes. *Drug Metab. Dispos.* 2006; 34: 1756-1763.

28. Adachi T., Nakagawa H., Chung I., Hagiya Y., Hoshijima K., Noguchi N., et al. Nrf2-dependent and -independent induction of ABC transporters ABCC1, ABCC2, and ABCG2 in HepG2 cells under oxidative stress. *J. Exp. Ther. Oncol.* 2007; 6: 335-348.

29. Van Aubel R. A., Smeets P. H., van den Heuvel J. J., Russel F. G. Human organic anion transporter MRP4 (ABCC4) is an efflux pump for the purine end metabolite urate with multiple allosteric substrate binding sites. *Am. J. Physiol. Renal Physiol.* 2005; 288: F327-F333.

30. Maher J. M., Dieter M. Z., Aleksunes L. M., Slitt A. L., Guo G., Tanaka Y., et al. Oxidative and electrophilic stress induces multidrug resistance-associated protein transporters via the nuclear factor-E2-related factor-2 transcriptional pathway. *Hepatology* 2007; 46:1597-1610.

31. Xu S., Weerachayaphorn J., Cai S. Y., Soroka C. J., Boyer J. L. Aryl hydrocarbon receptor and NF-E2-related factor 2 are key regulators of human MRP4 expression. *Am. J. Physiol. Gastrointest. Liver Physiol.* 2010; 299: G126-G135.

32. Aleksunes L. M., Goedken M. J., Rockwell C. E., Thomale J., Manautou J. E., Klaassen C. D. Transcriptional regulation of renal cytoprotective genes by Nrf2 and its potential use as a therapeutic target to mitigate cisplatin-induced nephrotoxicity. *J. Pharmacol. Exp. Ther.* 2010; 335: 2-12.

33. El-Sheikh A. A., van den Heuvel J. J., Koenderink J. B., Russel F. G. Effect of hypouricaemic and hyperuricaemic drugs on the renal urate efflux transporter, multidrug resistance protein 4. *Br. J. Pharmacol.* 2008; 155: 1066-1075.

34. Feher M. D., Hepburn A. L., Hogarth M. B., Ball S. G., Kaye S. A. Fenofibrate enhances urate reduction in men treated with allopurinol for hyperuricaemia and gout. *Rheumatology (Oxford)* 2003; 42: 321-325.

35. Hepburn A. L., Kaye S. A., Feher M. D. Fenofibrate: a new treatment for hyperuricaemia and gout? *Ann. Rheum. Dis.* 2001; 60: 984-986.

36. Kiyohara C., Kono S., Honjo S., Todoroki I., Sakurai Y., Nishiwaki M., et al. Inverse association between coffee drinking and serum uric acid concentrations in middle-aged Japanese males. *Br. J. Nutr.* 1999; 82: 125-130.

37. Choi H. K., Curhan G. Coffee, tea, and caffeine consumption and serum uric acid level: the Third National Health and Nutrition Examination Survey. *Arthritis Rheum.* 2007; 57: 816-821.

38. Choi H. K., Willett W., Curhan G. Coffee consumption and risk of incident gout in men a prospective study. *Arthritis Rheum.* 2007; 56: 2049-2055.

39. Balstad T. R., Carlsen H., Myhrstad M. C., Kolberg M., Reiersen H., Gilen L., et al. Coffee, broccoli and spices are strong inducers of electrophile response element-dependent transcription in vitro and in vivo—Studies in electrophile response element transgenic mice. *Mol. Nutr. Food Res.* 2011; 55:185497.

40. Boettler U., Sommerfeld K., Volz N., Pahlke G., Teller N., Somoza V., et al. Coffee constituents as modulators of Nrf2 nuclear translocation and ARE (EpRE)-dependent gene expression. *J. Nut. Biochem.* 2011; 22: 426-440.

41. Puig J. G., Martinez M. A. Hyperuricemia, gout and the metabolic syndrome. *Curr. Opin. Rheumatol.* 2008; 20: 187-191.

42. Inokuchi T., Tsutsumi Z., Takahashi S., Ka T., Moriwaki Y., Yamamoto T. Increased frequency of metabolic syndrome and its individual metabolic abnormalities in Japanese patients with primary gout. *J. Clin. Rheumatol.* 2010; 16: 109-112.

43. Fraile J. M., Puig J. G., Torres R. J., de Miguel E., Martínez P., Vázquez J. J. Uric acid metabolism in patients with primary gout and the metabolic syndrome. *Nucleosides Nucleotides Nucleic Acids.* 2010; 29: 330-334.
44. Yu Z, Shao W, Chiang Y, Foltz W, Zhang Z, Ling W, et al. Oltipraz upregulates the nuclear respiratory factor 2 alpha subunit (Nfr2) antioxidant system and prevents insulin resistance and obesity induced by a high-fat diet in C57BL/6J mice. *Diabetologia* 2011; 2011; 54: 922-934.
45. Shin S., Wakabayashi J., Yates M. S., Wakabayashi N., Dolan P. M., Aja S., et al. Role of Nrf2 in prevention of high-fat diet-induced obesity by synthetic triterpenoid CDDO-imidazolide. *Eur. J. Pharmacol.* 2009; 620: 138-144.
46. Zhou R., Tardivel A., Thorens B., Choi I., Tschopp J. Thioredoxin-interacting protein links oxidative stress to inflammasome activation. *Nat. Immunol.* 2010; 11: 136-140.
47. Tanito M., Agbaga M. P., Anderson R. E. Upregulation of thioredoxin system via Nrf2-antioxidant responsive element pathway in adaptive-retinal neuroprotection in vivo and in vitro. *Free Radic. Biol. Med.* 2007; 42: 1838-1850.
48. wwvv.urlpharma.com/url_unapproved_drug_Colcrys.aspx
49. Mallawista S. E., Seegmiller J. E. The effect of pretreatment with colchicine on the inflammatory response to microcrystalline urate: a model for gouty inflammation. *Ann. Intern. Med.* 1965; 62: 648-657.
50. Martinon F., Pétrilli V., Mayor A., Tardivel A., Tschopp J. Gout-associated uric acid crystals activate the NALP3 inflammasome. *Nature* 2006; 440: 237-241.
51. Stavric B., Clayman S., Gadd R. E., Hébert D. Some in vivo effects in the rat induced by chlorprothixene and potassium oxonate. *Pharmacol. Res. Commun.* 1975; 7: 117-24.
52. Hall I. H., Scoville J. P., Reynolds D. J., Simlot R., Duncan P. Substituted cyclimides as potential anti-gout agents. *Life Sci.* 1990; 46: 1923-1927.
53. Wang Y., Zhu J. X., Kong L. D., Yang C., Cheng C. H., Zhang X. Administration of procyanidins from grape seeds reduces serum uric acid levels and decreases hepatic xanthine dehydrogenase/oxidase activities in oxonate-treated mice. *Basic Clin. Pharmacol. Toxicol.* 2004; 94: 232-237.
54. Carroll J. J., Coburn H., Douglass R., Babson A. L. A simplified alkaline phosphotungstate assay for uric acid in serum. *Clin. Chem.* 1971; 17: 158-160.
55. Liu-Bryan R., Scott P., Sydlaske A., Rose D. M., Terkeltaub R. Innate immunity conferred by Toll-like receptors 2 and 4 and myeloid differentiation factor 88 expression is pivotal to monosodium urate monohydrate crystal-induced inflammation. *Arthritis Rheum.* 2005; 52: 2936-2946.
56. Ortiz-Bravo E., Schumacher H. R., Jr. Components generated locally as well as serum alter the phlogistic effect of monosodium urate crystals in vivo. *J. Rheumatol.* 1993; 20: 1162-1166.
57. So A., De Smedt T., Revaz S., Tschopp J. A pilot study of IL-1 inhibition by anakinra in acute gout. *Arthritis Res. Ther.* 2007; 92: R28.
58. Junnarkar S. P., Tapuria N., Mani A., Dijk S., Fuller B., Seifalian A. M., et al. Attenuation of warm ischemia-reperfusion injury in the liver by bucillamine through decreased neutrophil activation and Bax/Bcl2 modulation. *J. Gastroenterol. Hepatol.* 2010; 25: 1891-1899.
59. Ben-Chetrit E., Bergmann S., Sood R. Mechanism of the anti-inflammatory effect of colchicine in rheumatic diseases: a possible new outlook through microarray analysis. *Rheumatology (Oxford)* 2006; 45: 274-282.
60. Cronstein B. N., Molad Y., Reibman J., Balakhane E., Levin R. I., et al. Colchicine alters the quantitative and qualitative display of selectins on endothelial cells and neutrophils. *J. Clin. Invest.* 1995; 96: 994-1002.
61. Tsuji F., Miyake Y., Aono H., Kawashima Y., Mita S. Effects of bucillamine and N-acetyl-L-cysteine on cytokine production and collagen-induced arthritis (CIA). *Clin. Exp. Immunol.* 1999; 115: 26-31.
62. Terkeltaub R. A., Furst D. E., Bennett K., Kook K. A., Crockett R. S., Davis M. W. High versus low dosing of oral colchicine for early acute gout flare: Twenty-four-hour outcome of the first multicenter, randomized, double-blind, placebo-controlled, parallel-group, dose-comparison colchicine study. *Arthritis Rheum.* 2010; 62: 1060-1068.
63. Richette P., Bardin T. Colchicine for the treatment of gout. *Expert. Opin. Pharmacother.* 2010; 11: 2933-2938.

The invention claimed is:

1. A method for the treatment or prevention of gout, and/or the attenuation of metabolic syndrome in a mammal comprising administering a therapeutically effective amount of bucillamine or a pharmaceutically acceptable salt or solvate thereof to a mammal in need thereof.

2. The method according to claim 1, wherein the said method comprises administering between 25 mg and 8,000 mg of bucillamine or a pharmaceutically acceptable salt or solvate thereof.

3. The method according to claim 1, wherein the said method comprises administering between 400 mg and 4000 mg of bucillamine or a pharmaceutically acceptable salt or solvate thereof.

4. The method according to claim 1, wherein the said method comprises administering between 800 mg and 2000 mg of bucillamine or a pharmaceutically acceptable salt or solvate thereof.

5. The method according to claim 1, wherein the said method comprises administering between 800 mg and 4000 mg of bucillamine or a pharmaceutically acceptable salt or solvate thereof.

6. The method according to claim 1, wherein the method comprises administering between 900 mg and 1,800 mg of bucillamine or a pharmaceutically acceptable salt or solvate thereof.

7. The method as claimed in claim 1, further comprising administering a therapeutically effective amount of allopurinol or a pharmaceutically acceptable salt or solvate thereof to a mammal in need thereof.

8. The method according to claim 7, wherein the said method comprises administering between 200 mg and 800 mg of allopurinol or a pharmaceutically acceptable salt or solvate thereof.

9. The method according to claim 7 wherein the bucillamine or a pharmaceutically acceptable salt or solvate thereof and allopurinol or a pharmaceutically acceptable salt or solvate thereof are administered concurrently as a single dose once a day.

10. The method as claimed in claim 1, further comprising administering a therapeutically effective amount of colchicine or a pharmaceutically acceptable salt or solvate thereof, to a mammal in need thereof.

11. The method according to claim 10, wherein the said method comprises administering between 0.2 mg and 1.8 mg of colchicine or a pharmaceutically acceptable salt or solvate thereof.

12. The method according to claim 10 wherein the bucillamine or a pharmaceutically acceptable salt or solvate thereof and colchicine or a pharmaceutically acceptable salt or solvate thereof are administered concurrently as a single dose once a day.

13. The method according to claim 1, wherein said gout is an acute gout flare.

14. The method according to claim 1, wherein the said treatment or prevention of gout is treatment in mammals with metabolic syndrome.

* * * * *